United States Patent [19]
Terashima et al.

[11] Patent Number: 6,162,626
[45] Date of Patent: Dec. 19, 2000

[54] THERMOSTABLE GLUTAMATE DEHYDROGENASE AND PROCESS FOR PRODUCING THE SAME

[75] Inventors: Chikako Terashima; Kohji Uchida; Hirokazu Matsukawa; Osamu Oka; Tuyosi Fujita, all of Tokyo; Tadayuki Imanaka, Osaka, all of Japan

[73] Assignee: Oriental Yeast Co., Ltd., Tokyo, Japan

[21] Appl. No.: 09/239,303

[22] Filed: Jan. 29, 1999

[30] Foreign Application Priority Data

Jul. 31, 1998 [JP] Japan .................................. 10-217569

[51] Int. Cl.⁷ .............................. C12N 9/02; C12N 1/20; C12N 15/00; C07H 21/04
[52] U.S. Cl. .................. 435/189; 435/320.1; 435/252.3; 435/252.33; 536/23.2
[58] Field of Search ................................ 435/189, 320.1, 435/252.3, 252.33; 536/23.2

[56] References Cited

FOREIGN PATENT DOCUMENTS

| | | |
|---|---|---|
| 6-38744 | 2/1994 | Japan . |
| 6-327471 | 11/1994 | Japan . |
| 173078 | 7/1997 | Japan . |
| 252773 | 9/1997 | Japan . |

OTHER PUBLICATIONS

Consalvi et al Eur. J. Biochem. 202, p. 1189–1196 (1991).
Robb et al Biochimica et Biophysica Acta. 1120 (1992) p. 267–272.
Ohshima et al Biosci. Biotech. Biochem. 57 (6), p. 945–951 (1993).
Eggen et al Gene 132 (1993) p. 143–148.
Maras et al J. of Protein Chemistry, vol. 13, No. 2 (1994), p. 253–259.
DiRuggiero et al Applied and Environmental Microbiology, Jan. 1995 p. 159–164.
Kesen et al Applied and Environmental Microbiology, Feb. 1994, p. 562–568.
DiRuggiero J. Biological Chemistry, vol. 268, No. 24, p. 17767–17774 1993.
Rahman et al Biochem. biophys. Res. Commun. 241, p. 646–652 (1997).
ATCC Catalog, 3rd edition, p. 17, 1993.
Zhou et al., "Large scale production of recombinant mouse and rat growth hormone by fed–batch GS–NSO cell cultures", Cytotechnology 22:239–250, 1996.
Yang et al., "Production of recombinant human granulocyte––colony–stimulating factor in high cell density yeast cultures", Biotechnology Letters, vol. 19, No. 7, Jul. 1997, pp. 655–659.
Mendoza–Vega et al., "Recombinant outer–surface protein A (des–Cy1–OspA) from the Lyme disease spirochete *Borrelia burgdorferi*: high production levels in *Sacharomyces cerevisiae* yeast cultures", Appl. Microbiol. Biotechnol. (1996) 44: 624–628.

Fleer et al., "Stable Multicopy Vectors for High–Level Secretion of Recombinant Human Serum Albumin by *Kluyveromyces* Yeasts", bio/Technology vol. 9, Oct. 1991, 969–975.
Nakayama et al., "Efficient secretion of the authentic mature human growth hormone by *Bacillus subtilis*", Journal of Biotechnology, 8 (1988) 123–134.
Robinson et al., "Production of Engineered Antibodies in Myeloma and Hybridoma Cells", Department of Cellular and Molecular Biology, Merck Research Laboratories, Rahway, NJ 07065, pp. 1–14.
Nurmianto et al., "Optimal Feeding Policy for Recombinant Protein Production via the Yeast *Saccharomyces cerevisiae* in Fed–Batch Culture", Process Biochemistry, 29 (1994) 55–68.
Park et al., "Effect of Transcription Promoters on the Optimal Production of Secreted Protein in Fed–Batch Reactors", Biotechnology Progress, vol. 6, N0. 5, Sep./Oct. 1990, 311–318.
Lang et al., "Optimization of fungal polygalacturonase synthesis by *Saccharomyces cerevisiae* in fed–batch culture", Chemical Engineering Journal, 65 (1997) 219–226.
d'Anjou et al., "A model–based feeding strategy for fed––batch fermentation of recombinant *Pichia pastoris*", Biotechnology Techniques, vol. 11, No. 12, Dec. 1997, pp. 865–868.
Choi et al., "Effects of Medium Composition on Hirudin Production in Recombinant *Saccharomyces Cerevisiae*", Biotechnology Letters, vol. 18, No. 10, (Oct. 1996), pp. 1129–1132.
Chung et al., "Optimization of Feeding Strategy for Overproduction of Human Lipocortin–II *Saccharomyces cerevisiae* Controlled by the GAL10 Promoter", Journal of Fermentation and Bioengineering, vol. 84, No. 5, 466–470, 1997.
Chen et al., "High protein expression in fermentation of recombinant *Pichia pastoris* by a fed–batch process", Process Biochemistry, vol. 32, No. 2, pp. 107–111, 1997.
Ibba et al., "Mode of Cultivation is Critical for the Optimal Expression of Recombinant Hirudin by *Saccharomyces cerevisiae*", Biotechnology Letters, vol. 15, No. 7 (Jul. 1993), pp. 667–672.
Chang et al., "Enhancement of Rice α–Amylase Production in Recombinant *Yarrowia lipolytica*", Journal of Fermentation and Bioengineering, vol. 84, No. 5, 421–427, 1997.

(List continued on next page.)

*Primary Examiner*—Rebecca E. Prouty
*Assistant Examiner*—M. Monshipouri
*Attorney, Agent, or Firm*—Nixon & Vanderhye PC

[57] ABSTRACT

The present invention provides a process for mass producing recombinant, thermostable GLDH at a low cost. The invention also provides a process for mass producing recombinant, thermostable GLDH at a low cost, by culturing a transformant without using a drug such as IPTG. The invention further provides thermostable GLDH which can use more stable NADH as a coenzyme in an ammonia assay reagent.

7 Claims, 10 Drawing Sheets

OTHER PUBLICATIONS

Chiruvolu et al., "Recombinant protein production in an alcohol oxidase–defective strain of *Pichia pastoris* in fed-batch fermentations", Enzyme and Microbial Technology, 21, 277–283, 1997.

Narciandi et al., "High Level ProduCtion of Recombinant Invertase in *Hansenula polymorpha*", Biotechnology Letters, vol. 17, No. 9 (Sep. 1995), pp. 949–952.

Hardjito et al., "A Model for β–Galactosidase Production with a Recombinant Yeast *Saccharomyces cerevisiae* in fed–Batch Culture", Biotechnogy Progress, 1992, 9, 298–306.

Jin et al., "On the Development of Intelligent Control System for Recombinant Cell Culture", Methodologies for the Conception, Design, and Application of Intelligent Systems, Proceedings of IIZUKA '96, pp. 603–606.

Bédard et al., "Fed–batch culture of Sf–9 cells supports 3 x 10⁷ cells per ml and improves baculovirus–expressed recombinant protein yields", Biotechnology Letters, vol. 9, No. 7, Jul. 1997, pp. 629–632.

Fig. 1

```
Pfu    1 : MVEQDPYEIV IKQLERAAQY MEISEEALEF LKRPQRIVEV TIPVEMDDGS VKVFTGFRVQ
           *** ** *   *******    * *******   **** *****    ********  **********
KOD1   1 : MVEIDPFEMA VQQLERAAQF MDISEEALEW LKRPMRIVEV SVPVEMDDGS VKVFTGFRVQ

Pfu   61 : HNWARGPTKG GIRWHPEETL STVKALAAWM TWKTAVMDLP YGGGKGGIIV DPKKLSDREK
           **********  ****** *** ******* ** *** ** *** ********** ****** **
KOD1  61 : HNWARGPTKG GIRWHPAETL STVKALATWM TWKVAVVDLP YGGGKGGIIV DPKKLSEREQ

Pfu  121 : ERLARGYIRA IYDVISPYED IPAPDVYTNP QIMAWMMDEY ETISRRKTPA FGIITGKPLS
           ***** ****  **** *     * ********** *********  *** *** **  ** *****
KOD1 121 : ERLARSYIRA VYDVIGPCTD IPAPDVYTNP KIMAWMMDEY ETIMRRKGPA FGVITGKPPG

Pfu  181 : IGGSLGRIEA TARGASYTIR EAAKVLGWDT LKGKT IAIQG  YGNAGYYLAK IMSEDFGMKV
           **    *  *  *****  *** **** ****  ***** ***** ********  * **** *****
KOD1 181 : VGGIVARMDA TARGAAFTIR EAAKALGWDD LKGKT IAIQG  YGNAGYYLHK IMSEEFGMKV

Pfu  241 : VAVSD SKGGI YNPDGL-NAD EVLKWKNEHG SVKDFPGATN ITNEELLELE VDVLAPAAIE
           ***** ****** ******   ** ****** ***  **** **  *  ********** ** *** ***
KOD1 241 : VAVSD SKGGI YNPDGLPPAD EVLKWKKEHG SVKDMPGTQN ITNEELLELE VDILAPSAIE

Pfu  300 : EVITKKNADN IKAKIVAEVA NGPVTPEADE ILFEKGILQI PDFLCNAGGV TVSYFEWVQN
           **** ****  ********** **********  ** ******* ******  *** **********
KOD1 301 : GVITKENADN VKAKIVAEVA NGPVTPEADE ILHEKGILQI PDFLCNTGGV TVSYFEWVQN

Pfu  360 : ITGYYWTIEE VRERLDKKMT KAFYDVYNIA KEKNIHMRDA AYVVAVQRVY QAMLDRGWVK
           * ****  **  * *** ***  ***  ** *   **********  ***** ***   **    *****
KOD1 361 : INGFYWTVEE TRKRLDDKMT KAFWDVFNTH KEKNIHMRDA AYVVAVSRVY EAMKHRGWVK

Pfu  420 : H

KOD1 421 : K
```

Fig. 2

```
  1 :  ATGGTTGAGC AAGACCCCTA TGAAATTGTT ATTAAGCAAC TTGAAAGAGC TGCCCAATAT
        ***** ***    ***** *  *** ** *    *  **** * **** ** **  ****** *
  1 :  ATGGTCGAGA TTGACCCGTT TGAGATGGCC GTCCAGCAGC TTGAGAGGGC TGCCCAGTTC

61 :  ATGGAGATAA GTGAAGAAGC TCTTGAGTTC TTAAAGAGAC CTCAAAGAAT TGTTGAGGTC
        ***** ****  * ***** **  *******    * ***** * *    ** **  *********
 61 :  ATGGACATAA GCGAAGAGGC CCTTGAGTGG CTCAAGAGGC CCATGAGGAT TGTTGAGGTT

121 :  ACAATTCCAG TAGAAATGGA TGACGGTTCT GTAAAAGTTT TCACTGGATT TAGAGTACAA
        *  **** *   * ** *****  *********  ** ** **** **** ** **   * ** **
121 :  AGCGTTCCCG TCGAGATGGA CGACGGTTCT GTCAAGGTTT TCACCGGTTT CCGTGTCCAG

181 :  CACAACTGGG CTAGAGGTCC AACTAAGGGT GGAATTAGAT GGCATCCAGA AGAAACCCTT
       **********  *  *****  **  ******  ** **  **  *  **** ** *   ** *****
181 :  CACAACTGGG CCCGCGGTCC GACCAAGGGT GGTATAAGGT GGCACCCGGC CGAGACCCTC

241 :  AGCACTGTTA AAGCTCTTGC AGCTTGGATG ACATGGAAGA CTGCTGTAAT GGATCTCCCA
       **********  * **  *****   * ******  ** ******    *** **  *  ** *****
241 :  AGCACCGTTA AGGCCCTTGC CACCTGGATG ACCTGGAAGG TTGCCGTCGT TGACCTCCCC

301 :  TATGGTGGAG GTAAGGGTGG AATAATTGTA GATCCAAAGA AGCTCTCCCA CAGAGAGAAG
        ** *******  **********  ** ** **  ** ** **** **********  ** *** **
301 :  TACGGTGGAG GTAAGGGTGG CATCATCGTT GACCCGAAGA AGCTCTCCGA GAGGGAGCAG

361 :  GAGAGGCTTG CAAGAGGTTA CATTAGAGCA ATTTATGATG TTATTAGCCC ATATGAAGAC
        ********  *  **   * **  *** ** **    * ** ** * * **   ****  *     ***
361 :  GAGAGGCTCG CTAGGAGCTA CATAAGGGCC GTCTACGACG TCATCGGCCC GTGCACAGAT

421 :  ATTCCAGCAC CCGATGTTTA TACAAACCCA CAAATAATGG CATGGATGAT GGATGAGTAC
       ***** **  *  * ** *****  ** *****    *  ** **** *  ******* *** ******
421 :  ATTCCGGCCC CTGACGTTTA CACCAACCCG AAGATCATGG CCTGGATGAT GGACGAGTAC

481 :  GAGACAATAA GCAGGAGAAA GACACCGGCC TTTGGAATTA TCACTGGAAA GCCTCTTAGC
        ***** ****   ********  *   ****** ** **   * *  **** *****   *** *    *
481 :  GAGACCATAA TGAGGAGAAA GGGGCCGGCC TTCGGTGTCA TCACCGGAAA GCCGCCGGGA

541 :  ATTGGTGG-A TCACTTGGAA GAATTGAGGC AACTGCAAGA GGTGCAAGTT ACACAATTAG
       **** ***  *  **   *  *   * ****  ** **   ** **  **    *****   *   *** ** **
541 :  GTTGGCGGTA TC-GTCGCCA GAATGGACGC CACCGCTCGC GGTGCTGCCT TCACTATCAG
```

Fig. 3

```
 600: AGAGGCTGCA AAGGTTCTTG GATGGGACAC CCTCAAGGGC AAGACAATAG CAATCCAGGG
      ** ** **   ****  ** *  * ******   **********  ***** ****  * ********
 600: GGAAGCCGCT AAGGCCCTCG GCTGGGACGA CCTCAAGGGC AAGACCATAG CCATCCAGGG

660: TTACGGTAAC GCGGGTTATT ATCTTGCAAA GATCATGAGT GAAGACTTTG GAATGAAGGT
      *********  ** ** **  *  * **    **  *** ****** ** ** ** *  * ********
 660: CTACGGTAAC GCCGGCTACT ACCTCCACAA GATAATGAGT GAGGAGTTCG GTATGAAGGT

720: TGTAGCTGTG AGCGACAGCA AGGGTGGAAT ATACAACCCC GATGGTCT-- -TAATGCTGA
      ** ** **   **********  **** ** **  ********  ** ** ****           *****
 720: CGTTGCCGTC AGCGACAGCA AGGGCGGCAT CTACAACCCG GACGGGCTCC CGCCGGCTGA

777: CGAGGTTCTC AAGTGGAAGA ATGAGCATGG AAGCGTTAAA GACTTCCAG GAGCAACCAA
      ****** *** **********  * ***** **          ** ** *** * ** * ** *       **
 780: CGAGGTACTC AAGTGGAAGA AGGAGCACGG CTCAGTCAAG GACATGCCCG GAACCCAGAA

837: CATAACGAAT GAGGAGCTAC TTGAGCTTGA GGTTGATGTT CTCGCTCCGG CAGCTATAGA
      *** ** **  ******** *  * ********  ** **   *  ** ** ***   ** ** **
 840: CATCACCAAC GAGGAGCTCC TCGAGCTTGA AGTCGACATC CTTGCCCCGA GCGCCATCGA

897: AGAAGTGATA ACTAAGAAGA ACGCAGACAA CATTAAGGCT AAGATCGTTG CAGAAGTAGC
      *  ** ***  ** ** ***  **** *****  * * *****  ********  * * ** *****
 900: GGGCGTCATA ACCAAAGAGA ACGCCGACAA CGTCAAGGCC AAGATCGTCG CCGAGGTAGC

957: AAACGGTCCA GTTACTCCAG AAGCTGATGA GATACTATTC GAGAAAGGAA TCCTTCAGAT
      ********  ** ** ** *  * ** ** **  ******   * ***** ** *  **** *****
 960: CAACGGTCCG GTCACCCCGG AGGCCGACGA GATACTCCAC GAGAAGGGCA TCCTCCAGAT

1017: CCCAGACTTC CTATGTAATG CTGGTGGAGT TACAGTCAGC TACTTCGAGT GGGTACAGAA
      *** ******  ** *****  * ***** **  ** ******  ********** **** *****
1020: CCCGGACTTC CTCTGTAACA CCGGTGGTGT CACCGTCAGC TACTTCGAGT GGGTCCAGAA

1077: CATAACTGGA TACTACTGGA CAATTGAGGA GGTTAGAGAG AGACTCGACA AGAAGATGAC
      *****  **  * ********  *  * ***** *  ** **  ** ******  * ********
1080: CATAAACGGC TTCTACTGGA CGGTCGAGGA GACCAGGAAG AGGCTCGACG ACAAGATGAC

1137: AAAAGCATTC TACGACGTCT ACAACATAGC AAAGGAGAAG AACATACACA TGAGAGATGC
      ** ******  * *******   *****    *********  ***** ****  **** ** **
1140: CAAGGCATTC TGGGACGTCT TCAACACCCA CAAGGAGAAG AACATCCACA TGAGGGACGC

1197: AGCTTACGTA GTTGCAGTCC AGAGAGTTTA TCAAGCAATG CTTGACCGTG GATGGGTCAA
      ** *****   ***** ***  ** ** **  * ******    **** * *******  **
1200: TGCCTACGTC GTTGCCGTCA GCAGGGTCTA CGAGGCAATG AAGCACCGCG GATGGGTGAA

1257: GCACTGA
      *  ***
1260: GAAGTGA
```

●, ▲ : KOD1-GLDH WAS USED (PRESENT INVENTION)

○, △ : YEAST-GLDH WAS USED (CONTROL)

SEQUENCE LISTING

```
<160> NUMBER OF SEQ ID NOS: 10

<210> SEQ ID NO 1
<211> LENGTH: 1380
<212> TYPE: DNA
<213> ORGANISM: Pyrococcus sp.
<220> FEATURE:
<223> OTHER INFORMATION: KOD1

<400> SEQUENCE: 1
ttgttcaaaa cagactgttt tccagcctgt ttatcgaaag gtttatatat gcaaacgcct      60
aaggaaacag ctatgaccat gattaccgaa atgagctggt atgaatggtc gagattgacc     120
cgtttgagat ggccgtccag cagcttgaga gggctgccca gttcatggac ataagcgaag    180
aggcccttga gtggctcaag aggcccatga ggattgttga ggttagcgtt cccgtcgaga    240
tggacgacgg ttctgtcaag gttttcaccg gtttccgtgt ccagcacaac tgggcccgcg    300
gtccgaccaa gggtggtata aggtggcacc cggccgagac cctcagcacc gttaaggccc    360
ttgccacctg gatgacctgg aaggttgccg tcgttgacct ccgctacggt ggaggtaagg    420
gtggcatcat cgttgacccg aagaagctct ccgagaggga gcaggagagg ctcgctagga    480
```

-continued

```
gctacataag ggccgtctac gacgtcatcg gcccgtgcac agatattccg gcccctgacg    540
tttacaccaa cccgaagatc atggcctgga tgatggacga gtacgagacc ataatgagga    600
gaaaggggcc ggccttcggt gtcatcaccg gaaagccgcc gggagttggc ggtatcgtcg    660
ccagaatgga cgccaccgct cgcggtgctg ccttcactat cagggaagcc gctaaggccc    720
tcggctggga cgacctcaag gcaagacca tagccatcca gggctacggt aacgccggct     780
actacctcca caagataatg agtgaggagt tcggtatgaa ggtcgttgcc gtcagcgaca    840
gcaagggcgg catctacaac ccggacgggc tcccgccggc tgacgaggta ctcaagtgga    900
agaaggagca cggctcagtc aaggacatgc ccggaaccca gaacatcacc aacgaggagc    960
tcctcgagct tgaagtcgac atccttgccc gagcgccat cgagggcgtc ataaccaaag     1020
agaacgccga caacgtcaag gccaagatcg tcgccgaggt agccaacggt ccggtcaccc    1080
cggaggccga cgagatactc cacgagaagg gcatcctcca gatcccggac ttcctctgta    1140
acaccggtgg tgtcaccgtc agctacttcg agtgggtcca gaacataaac ggcttctact    1200
ggacggtcga ggagaccagg aagaggctcg acgacaagat gaccaaggca ttctgggacg    1260
tcttcaacac ccacaaggag aagaacatcc acatgaggga cgctgcctac gtcgttgccg    1320
tcagcagggt ctacgaggca atgaagcacc gcggatgggt gaagaagtga tttcttctcc    1380
```

<210> SEQ ID NO 2
<211> LENGTH: 421
<212> TYPE: PRT
<213> ORGANISM: Pyrococcus sp.
<220> FEATURE:
<223> OTHER INFORMATION: KOD1

<400> SEQUENCE: 2

```
Met Val Glu Ile Asp Pro Phe Glu Met Ala Val Gln Gln Leu Glu Arg
 1               5                  10                  15

Ala Ala Gln Phe Met Asp Ile Ser Glu Glu Ala Leu Glu Trp Leu Lys
             20                  25                  30

Arg Pro Met Arg Ile Val Glu Val Ser Val Pro Val Glu Met Asp Asp
         35                  40                  45

Gly Ser Val Lys Val Phe Thr Gly Phe Arg Val Gln His Asn Trp Ala
     50                  55                  60

Arg Gly Pro Thr Lys Gly Gly Ile Arg Trp His Pro Ala Glu Thr Leu
 65                  70                  75                  80

Ser Thr Val Lys Ala Leu Ala Thr Trp Met Thr Trp Lys Val Ala Val
                 85                  90                  95

Val Asp Leu Pro Tyr Gly Gly Gly Lys Gly Gly Ile Ile Val Asp Pro
            100                 105                 110

Lys Lys Leu Ser Glu Arg Glu Gln Glu Arg Leu Ala Arg Ser Tyr Ile
        115                 120                 125

Arg Ala Val Tyr Asp Val Ile Gly Pro Cys Thr Asp Ile Pro Ala Pro
    130                 135                 140

Asp Val Tyr Thr Asn Pro Lys Ile Met Ala Trp Met Asp Glu Tyr
145                 150                 155                 160

Glu Thr Ile Met Arg Arg Lys Gly Pro Ala Phe Gly Val Ile Thr Gly
                165                 170                 175

Lys Pro Pro Gly Val Gly Gly Ile Val Ala Arg Met Asp Ala Thr Ala
            180                 185                 190

Arg Gly Ala Ala Phe Thr Ile Arg Glu Ala Ala Lys Ala Leu Gly Trp
        195                 200                 205
```

```
Asp Asp Leu Lys Gly Lys Thr Ile Ala Ile Gln Gly Tyr Gly Asn Ala
    210                 215                 220

Gly Tyr Tyr Leu His Lys Ile Met Ser Glu Glu Phe Gly Met Lys Val
225                 230                 235                 240

Val Ala Val Ser Asp Ser Lys Gly Gly Ile Tyr Asn Pro Asp Gly Leu
                245                 250                 255

Pro Pro Ala Asp Glu Val Leu Lys Trp Lys Lys Glu His Gly Ser Val
            260                 265                 270

Lys Asp Met Pro Gly Thr Gln Asn Ile Thr Asn Glu Glu Leu Leu Glu
        275                 280                 285

Leu Glu Val Asp Ile Leu Ala Pro Ser Ala Ile Glu Gly Val Ile Thr
    290                 295                 300

Lys Glu Asn Ala Asp Asn Val Lys Ala Lys Ile Val Ala Glu Val Ala
305                 310                 315                 320

Asn Gly Pro Val Thr Pro Glu Ala Asp Glu Ile Leu His Glu Lys Gly
                325                 330                 335

Ile Leu Gln Ile Pro Asp Phe Leu Cys Asn Thr Gly Gly Val Thr Val
            340                 345                 350

Ser Tyr Phe Glu Trp Val Gln Asn Ile Asn Gly Phe Tyr Trp Thr Val
    355                 360                 365

Glu Glu Thr Arg Lys Arg Leu Asp Asp Lys Met Thr Lys Ala Phe Trp
370                 375                 380

Asp Val Phe Asn Thr His Lys Glu Lys Asn Ile His Met Arg Asp Ala
385                 390                 395                 400

Ala Tyr Val Val Ala Val Ser Arg Val Tyr Glu Ala Met Lys His Arg
                405                 410                 415

Gly Trp Val Lys Lys
            420

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 3
aagcarcttg aragagctgc ccaata                                    26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 4
gtrtaaacrt crggtgctgg ratgtc                                    26

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 5
tgaaagaagg agatatccat ggtcgagatt gacccgtttg a                   41
```

-continued

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 6
aaagggatcc gaaatcactt cttcaccca                                         29

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 7
gaattcatgt atcgcgattt aaataaggag gaataaccca tgg                         43

<210> SEQ ID NO 8
<211> LENGTH: 1263
<212> TYPE: DNA
<213> ORGANISM: Pyrococcus furiosus

<400> SEQUENCE: 8
atggttgagc aagacccta tgaaattgtt attaagcaac ttgaaagagc tgcccaatat         60
atggagataa gtgaagaagc tcttgagttc ttaaagagac tcaaagaat tgttgaggtc        120 acaattccag tagaaatgga tgacggttct gtaaaagttt tcactggatt tagagtacaa      180
cacaactggg ctagaggtcc aactaagggt ggaattagat ggcatccaga agaaaccctt      240
agcactgtta agctcttgc agcttggatg acatggaaga ctgctgtaat ggatctccca      300
tatggtggag gtaagggtgg aataattgta gatccaaaga agctctccca cagagagaag      360
gagaggcttg caagaggtta cattagagca attttatgatg ttattagccc atatgaagac    420
attccagcac ccgatgttta tacaaaccca caaataatgg catggatgat ggatgagtac     480
gagacaataa gcaggagaaa gacaccggcc tttggaatta tcactggaaa gcctcttagc     540
attggtggat cacttggaag aattgaggca actgcaagag gtgcaagtta cacaattaga     600
gaggctgcaa aggttcttgg atgggacacc ctcaagggca agacaatagc aatccagggt    660
tacggtaacg cgggttatta tcttgcaaag atcatgagtg aagactttgg aatgaaggtt   720
gtagctgtga gcgacagcaa gggtggaata tacaaccccg atggtcttaa tgctgacgag   780
gttctcaagt ggaagaatga gcatggaagc gttaaagact ccccaggagc aaccaacata   840
acgaatgagg agctacttga gcttgaggtt gatgttctcg ctccggcagc tatagaagaa   900
gtgataacta gaagaacgc agacaacatt aaggctaaga tcgttgcaga gtagcaaac    960 ggtccagtta ctccagaagc tgatgagata ctattcgaga aggaatcct tcagatccca  1020 gacttcctat gtaatgctgg tggagttaca gtcagctact tcgagtgggt acagaacata  1080
actggatact actggacaat tgaggaggtt agagagagac tcgacaagaa gatgacaaaa  1140
gcattctacg acgtctacaa catagcaaag gagaagaaca tacacatgag agatgcagct  1200
tacgtagttg cagtccagag agtttatcaa gcaatgcttg accgtggatg ggtcaagcac  1260
tga                                                                 1263

<210> SEQ ID NO 9
<211> LENGTH: 420
<212> TYPE: PRT

<213> ORGANISM: Pyrococcus furiosus

<400> SEQUENCE: 9

Met Val Glu Gln Asp Pro Tyr Glu Ile Val Ile Lys Gln Leu Glu Arg
 1               5                  10                  15

Ala Ala Gln Tyr Met Glu Ile Ser Glu Ala Leu Glu Phe Leu Lys
            20                  25                  30

Arg Pro Gln Arg Ile Val Glu Val Thr Ile Pro Val Glu Met Asp Asp
            35                  40                  45

Gly Ser Val Lys Val Phe Thr Gly Phe Arg Val Gln His Asn Trp Ala
        50                  55                  60

Arg Gly Pro Thr Lys Gly Gly Ile Arg Trp His Pro Glu Glu Thr Leu
65                  70                  75                  80

Ser Thr Val Lys Ala Leu Ala Ala Trp Met Thr Trp Lys Thr Ala Val
                85                  90                  95

Met Asp Leu Pro Tyr Gly Gly Gly Lys Gly Gly Ile Ile Val Asp Pro
            100                 105                 110

Lys Lys Leu Ser Asp Arg Glu Lys Glu Arg Leu Ala Arg Gly Tyr Ile
            115                 120                 125

Arg Ala Ile Tyr Asp Val Ile Ser Pro Tyr Glu Asp Ile Pro Ala Pro
130                 135                 140

Asp Val Tyr Thr Asn Pro Gln Ile Met Ala Trp Met Met Asp Glu Tyr
145                 150                 155                 160

Glu Thr Ile Ser Arg Arg Lys Thr Pro Ala Phe Gly Ile Ile Thr Gly
                165                 170                 175

Lys Pro Leu Ser Ile Gly Gly Ser Leu Gly Arg Ile Glu Ala Thr Ala
            180                 185                 190

Arg Gly Ala Ser Tyr Thr Ile Arg Glu Ala Ala Lys Val Leu Gly Trp
        195                 200                 205

Asp Thr Leu Lys Gly Lys Thr Ile Ala Ile Gln Gly Tyr Gly Asn Ala
210                 215                 220

Gly Tyr Tyr Leu Ala Lys Ile Met Ser Glu Asp Phe Gly Met Lys Val
225                 230                 235                 240

Val Ala Val Ser Asp Ser Lys Gly Gly Ile Tyr Asn Pro Asp Gly Leu
                245                 250                 255

Asn Ala Asp Glu Val Leu Lys Trp Lys Asn Glu His Gly Ser Val Lys
            260                 265                 270

Asp Phe Pro Gly Ala Thr Asn Ile Thr Asn Glu Glu Leu Leu Glu Leu
        275                 280                 285

Glu Val Asp Val Leu Ala Pro Ala Ala Ile Glu Glu Val Ile Thr Lys
290                 295                 300

Lys Asn Ala Asp Asn Ile Lys Ala Lys Ile Val Ala Glu Val Ala Asn
305                 310                 315                 320

Gly Pro Val Thr Pro Glu Ala Asp Glu Ile Leu Phe Glu Lys Gly Ile
                325                 330                 335

Leu Gln Ile Pro Asp Phe Leu Cys Asn Ala Gly Gly Val Thr Val Ser
            340                 345                 350

Tyr Phe Glu Trp Val Gln Asn Ile Thr Gly Tyr Tyr Trp Thr Ile Glu
        355                 360                 365

Glu Val Arg Glu Arg Leu Asp Lys Lys Met Thr Lys Ala Phe Tyr Asp
370                 375                 380

Val Tyr Asn Ile Ala Lys Glu Lys Asn Ile His Met Arg Asp Ala Ala
385                 390                 395                 400

-continued

```
Tyr Val Val Ala Val Gln Arg Val Tyr Gln Ala Met Leu Asp Arg Gly
            405                 410                 415

Trp Val Lys His
            420

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: DNA
      construct

<400> SEQUENCE: 10
gaattcgtgc tcggtacccg gggatcctct agagtcgac                                    39
```

THERMOSTABLE GLUTAMATE DEHYDROGENASE AND PROCESS FOR PRODUCING THE SAME

BACKGROUND OF THE INVENTION

The present invention relates to thermostable glutamate dehydrogenase which is stable in an alkaline solution, and a process for its mass production. This invention also relates to glutamate dehydrogenase which can utilize $NAD^+$, a more stable coenzyme, as a coenzyme to be involved in a reaction, and an ammonia assay kit using such glutamate dehydrogenase.

Glutamate dehydrogenase (hereinafter referred to as "GLDH") is an enzyme which catalyzes a reaction of the following formula (1):

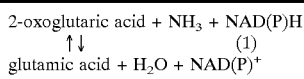

$$\text{2-oxoglutaric acid} + NH_3 + NAD(P)H \rightleftarrows \text{glutamic acid} + H_2O + NAD(P)^+ \quad (1)$$

This enzyme is widely distributed among animals, plants and microorganisms. So far, there has been known GLDH of various origins, including bacteria of the genera Proteus, Bacillus and Thermococcus. As an enzyme for applications such as determination of glutamic acid and clinical diagnosis, GLDH has attracted marked attention in recent years in the fields of biochemistry and medicine. The enzymatic activity of GLDH catalyzes the reaction of formula (1) in both directions. In the downward reaction by GLDH, ammonia is used as one of the reactants. Thus, ammonia in a sample produced from an in vivo substance and/or the in vivo substance in a sample can be quantitatively determined by use of this enzyme.

Recent years have seen a tendency toward the replacement of many assay reagent compositions for laboratory examination in a lyophilized powdery form by those in the form of a solution. This replacement is intended to omit the step of converting the powdery assay reagent composition to a solution each time it is to be used, thus reducing the burden on laboratory technicians. In developing a liquid reagent containing GLDH, use of an alkaline solution is required for ensuring stability of NAD(P)H (reduced nicotinamide adenine dinucleotide (phosphate)) which functions as a coenzyme in the reagent. Such use of an alkaline solution, however, has proved defective in that GLDH is deactivated rapidly, and long-term storage of the reagent is difficult. Furthermore, the reagent available is not suitable for long-term storage, as it is susceptible in terms of enzyme stability to accidental temperature changes.

We, the inventors of the present invention, have shown that thermostable GLDH originating from *Pyrococcus furiosus* has excellent stability under temperature changes during storage, and is stabile in an alkaline solution, and have disclosed that this GLDH can maintain high enzymatic activity in solution for a long period of time (Japanese Patent Application No. 310768/97).

Using conventional methods, however, the production cost of recombinant GLDH is high. There are a number of reasons for this. That is, the expression of recombinant GLDH has required that the expression of a recombinant gene be induced by the use of a drug (isopropyl-β-D(-)-thiogalactopyranoside; IPTG). In addition, the output of GLDH per wet weight of the bacterial cells has been low, and consequently the productivity of culture has also been low. Due to the above-mentioned induction by the drug, moreover, there has been no choice but to obtain a transformant by batch culture. These restrictions have resulted in continuing high manufacturing costs. In addition, thermostable GLDH of the *Pyrococcus furiosus* origin has been unable to utilize NADH, a more stable coenzyme, with the result that this enzyme has been unsuitable for the production of a reagent kit which is stable during long-term storage.

To overcome the foregoing drawbacks, it has been necessary to search for GLDH which has selectivity for NADH as a coenzyme. There has been a need to develop a process which enables large scale culture by the use of such GLDH, but without the use of a drug for induction of expression. However, no method for mass production of GLDH has hitherto been known, nor has such a preferred enzyme been known. Hence, the aforementioned problems have remained unsolved.

SUMMARY OF THE INVENTION

It is an object of the present invention to provide recombinant GLDH which can utilize more stable NADH as a coenzyme in an ammonia assay reagent, and which is stable even in an alkaline solution. Another object of the invention is to provide a process for producing the recombinant GLDH at low cost and on a large scale. Still another object of the invention is to provide a process for mass producing the recombinant GLDH at low cost by culturing a transformant without using a drug such as IPTG as stated earlier.

According to a first aspect of the present invention for attaining the foregoing objects, there is provided a process for producing of a recombinant glutamate dehydrogenase protein by large scale culture, which comprises performing fed-batch culture of a transformant, while continuously controlling the concentration of dissolved oxygen and/or continuously adding assimilable sources, vitamins and nitrogen sources such as amino acids, the transformant resulting from transformation with a recombinant glutamate dehydrogenase gene.

The glutamate dehydrogenase gene may be a thermostable glutamate dehydrogenase gene. The thermostable glutamate dehydrogenase gene may originate from Pyrococcus sp. KOD1 strain. The transformant may be prepared by transformation with a pTRP plasmid incorporating the recombinant glutamate dehydrogenase gene.

According to a second aspect of the invention, there is provided thermostable glutamate dehydrogenase derived from Pyrococcus sp. and capable of using reduced nicotinamide adenine dinucleotide (NADH) as a coenzyme.

The thermostable glutamate dehydrogenase may be derived from Pyrococcus sp. KOD1 strain. The thermostable glutamate dehydrogenase may have an amino acid sequence designated as SEQ ID No. 2 of a sequence listing.

According to a third aspect of the invention, there is provided a thermostable glutamate dehydrogenase gene encoding the thermostable glutamate dehydrogenase.

According to a fourth aspect of the invention, there is provided a thermostable glutamate dehydrogenase gene encoding the thermostable glutamate dehydrogenase having the amino acid sequence designated as SEQ ID No. 2.

The thermostable glutamate dehydrogenase gene may be isolated from Pyrococcus sp. KOD1 strain. The thermostable glutamate dehydrogenase gene may have a nucleotide sequence designated as SEQ ID No. 1 of the sequence listing.

According to a fifth aspect of the invention, there is provided a high expression pTRP plasmid having a thermostable glutamate dehydrogenase gene joined thereto, which can express the thermostable glutamate dehydrogenase by joining a nucleotide sequence of the thermostable glutamate dehydrogenase gene so as to be capable of functioning.

According to a sixth aspect of the invention, there is provided *Escherichia coli* transformed with the plasmid so as to express recombinant glutamate dehydrogenase in a large amount.

According to a seventh aspect of the invention, there is provided a reagent kit for assay of ammonia generated from an in vivo substance, the reagent kit containing the thermostable glutamate dehydrogenase.

The reagent kit may contain NADH as a coenzyme.

BRIEF DESCRIPTION OF THE DRAWINGS

The present invention will become clearer from the detailed description given hereinbelow taken with the accompanying drawings which are given by way of illustration only, and thus are not limitative of the present invention, and wherein:

FIG. 1 is a view showing a comparison between the amino acid sequence of KOD1-GLDH and the amino acid sequence of Pfu-GLDH, in which a portion surrounded by a rectangle is a site presumed to be a coenzyme binding site;

FIG. 2 is a view showing a comparison between the base sequence of KOD1-GLDH and the base sequence of Pfu-GLDH, each base sequence ranging from the 1st base to the 599th base;

FIG. 3 is a view showing a comparison between the base sequence of KOD1-GLDH and the base sequence of Pfu-GLDH, the base sequence of KOD1-GLDH ranging from the 600th base to the 1266th base;

DETAILED DESCRIPTION OF THE INVENTION

Figure 4:
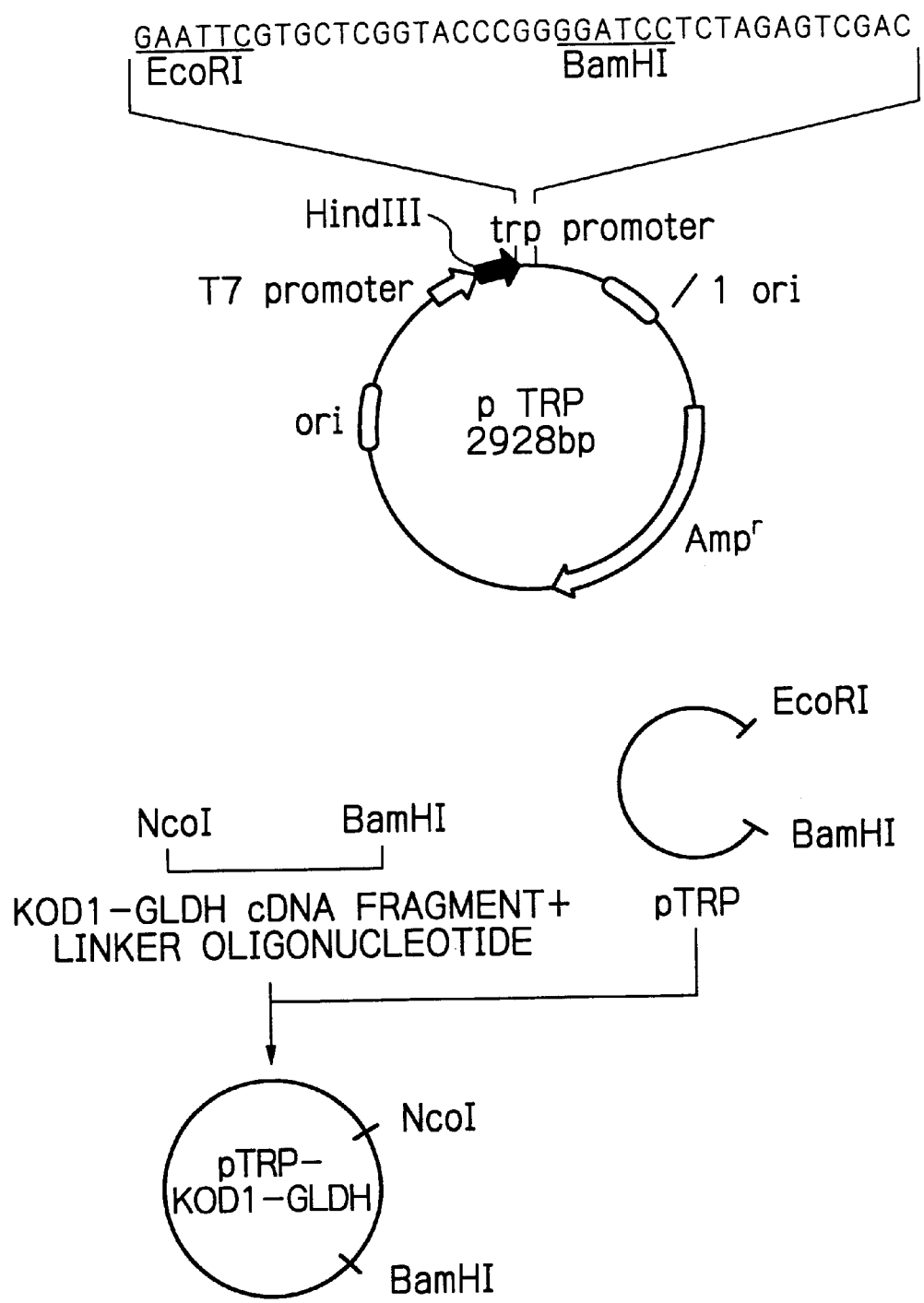
FIG. 4 shows the outline of a method for preparation of pTRP incorporating KOD1-GLDH gene.

GLDH is an enzyme which catalyzes a reaction for oxidizing glutamic acid to form 2-oxoglutaric acid and ammonia, as shown by the aforementioned formula (1). GLDH is classified into a type which specifically uses $NAD^+$ (oxidized nicotinamide adenine dinucleotide) as a coenzyme, a type which specifically uses $NADP^+$ (oxidized nicotinamide adenine dinucleotide phosphate) as a coenzyme, and a type which has reactivity with both of $NAD^+$ and $NADP^+$. However, the type of GLDH that is thermostable and utilizes $NAD^+$ is not known.

We have conducted studies in an attempt to solve the aforesaid problems. These studies have led to the finding that among microorganisms of the genus Pyrococcus is a strain producing GLDH which is thermostable and which can utilize $NAD^+$ as a coenzyme. That is, we have demonstrated that thermostable GLDH from Pyrococcus sp. KOD1 strain (the strain deposited at the National Institute of Bioscience and Human Technology, Japan, with the accession number FERM P-15007) (the GLDH will be referred to herein as KOD1-GLDH) is stable under temperature changes during storage, as well as being stable in an alkaline solution, and maintains high enzymatic activity in solution for a long period of time. We have also found that in comparison with thermostable GLDH from Pyrococcus furiosus (e.g. FERM BP-6159) (the GLDH is designated herein as Pfu-GLDH), KOD1-GLDH is reactive with $NAD^+$ which Pfu-GLDH cannot utilize as a coenzyme.

The gene of the present invention for KOD1-GLDH can be isolated by various methods. For example, genomic DNA is prepared from Pyrococcus sp. KOD1 strain that has been anaerobically cultured at 85° C. in a sulfur-containing culture medium. Polymerase chain reaction is performed using two types of degenerate primers, i.e., 5'-AAGCA(A/G) CTTG A(A/G)AGAGCTGC CCAATA-3' (forward primer, SEQ ID No. 3) and 5'-GT(A/G)TAAAC(A/G)T C(G/A) GGTGCTGG (A/G)ATGTC-3' (reverse primer, SEQ ID No. 4), whereby a targeted KOD1-GLDH gene fragment can be amplified from the genomic DNA. These primers are designed based on a highly homologous portion of the amino acid sequence of GLDH from other previously reported archaebacteria, and the sequence of Pfu-GLDH gene. Of these primers, the forward primer is designed as an oligonucleotide corresponding to KQLERAAQY ranging from the 12th amino acid to the 20th amino acid of Pfu-GLDH, while the reverse primer is designed as an oligonucleotide corresponding to DIPAPDVY ranging from the 140th amino acid to the 147th amino acid of Pfu-GLDH. The conditions for the PCR reaction can be determined, as required, by a person of ordinary skill in the art. For example, 30 cycles of the reaction are performed, with each cycle comprising denaturation for 60 seconds at 98° C., annealing for 30 seconds at 55° C., and polymerization for 60 seconds at 74° C. Then, 29 cycles of the reaction are performed, with each cycle comprising denaturation for 15 seconds at 98° C., annealing for 2 seconds at 55° C., and polymerization for 30 seconds at 72° C. The PCR amplification product is used as a probe to identify the targeted GLDH gene from the genomic DNA library of KOD1 by Southern hybridization. Then, PCR is performed by utilizing the resulting genomic DNA fragment as the template and using a forward primer containing a site for the restriction enzyme NcoI (5'-TGAAAGAAGG AGATATCCAT GGTC-GAGATT GACCCGTTTG A-3', SEQ ID No. 5) and a reverse primer containing a site for the restriction enzyme BamHI (5'-AAAGGGATCC GAAATCACTT CTTCACCCA-3', SEQ ID No. 6). As a result, a KOD1-GLDH gene fragment having NcoI/BamHI restriction enzyme sites at both ends is prepared. The PCR reaction is carried out in 30 cycles, with each cycle comprising denaturation for 60 seconds at 98° C., annealing for 30 seconds at 55° C., and polymerization for 60 seconds at 74° C. The thus obtained GLDH gene is then subjected to Sanger's dideoxy-mediated termination method using an automatic DNA sequencing system to analyze the sequence amplified by the foregoing method. In this manner, KOD1-GLDH gene comprising a DNA sequence shown as SEQ ID No. 1 can be obtained.

The amino acid sequence and base sequence of the KOD1-GLDH gene obtained by the above-described method are compared with the amino acid sequence and base sequence of Pfu-GLDH gene (R. I. L. Eggen et al., Gene, 132(1993), p.143–148) in FIGS. 1, 2 and 3. The results of analysis of the amino acid sequences show KOD1-GLDH to differ from Pfu-GLDH in that amino acid substitution occurs at two locations in the region ranging from $Ile^{216}$ to $Asp^{245}$, a region presumed to a pyridine nucleotide binding site (FIG. 1). Comparison of the entire sequence shows that homology for amino acids is calculated at 83.6% (FIG. 1). The discrepancy in responsiveness to the coenzyme $NAD^{30}$ that exists between KOD1-GLDH and Pfu-GLDH is considered to result from this difference in sequence.

To express the KOD1-GLDH gene obtained by the above method, this gene is introduced into a high expression plasmid. A plasmid which can be used to construct a high expression system, preferably, has a tryptophan promoter. The preferred plasmid is pTRP. Plasmid pTRP is an expression vector having a tryptophan promoter (trp promoter) which has been prepared based on plasmid pTZ19U by a previously disclosed method (Japanese Patent Public Disclosure: No. 252773/97). The pTRP can induce high expression without inducing expression by IPTG. Thus, the pTRP has the advantage lacking in other plasmids that the expression product of the gene can be obtained at a low cost. A transformant produced by transformation with the pTRP plasmid is described as being capable of high density culture as compared with transformants produced using other plasmids (Japanese Patent Public Disclosure: No. 252773/97).

A method for preparation of plasmid pTRP incorporating a KOD1-GLDH gene fragment is outlined in FIG. 4. Plasmid pTRP is treated with the restriction enzymes EcoRI and BamHI to prepare a restriction enzyme treated plasmid fragment having EcoRI-BamHI cleavage sites. A KOD1-GLDH gene fragment is incorporated into this restriction enzyme treated plasmid fragment. As stated earlier, the KOD1-GLDH gene fragment that has been amplified is a DNA fragment about 1.4 kbp long which has an NcoI restriction enzyme site and a BamHI restriction enzyme site at each end, respectively. To join this gene fragment to the restriction enzyme treated plasmid, a linker oligonucleotide having the sequence 5'-GAATTCATGT ATCGCGATTT AAATAAGGAG GAATAACCCA TGG-3' (SEQ ID No. 7) and having an EcoRI restriction enzyme site and an NcoI restriction enzyme site at each end, respectively, is synthesized and combined with the KOD1-GLDH gene fragment. This linker oligonucleotide has the sequence CCATGG, which is the NcoI restriction enzyme site, at the 3'-terminal, and the sequence GAATTC, which is the EcoRI restriction enzyme site, at the 5'-terminal. When this linker oligonucleotide and the KOD1-derived GLDH gene fragment are bonded together at the NcoI restriction enzyme site, therefore, the linker-KOD1-GLDH gene combined fragment has the EcoRI restriction enzyme site and the BamHI restriction enzyme site at each end, respectively. The thus prepared linker-KOD1-GLDH gene combined fragment is treated with EcoRI and BamHI restriction enzymes to prepare an EcoRI-BamHI fragment, which can be bound to the EcoRI-BamHI restriction enzyme treated plasmid fragment. Alternatively, the NcoI-BamHI restriction enzyme treated KOD1-GLDH gene fragment, the EcoRI-NcoI restriction enzyme treated linker, and the EcoRI-BamHI restriction enzyme treated plasmid fragment can be mixed, and ligated together simultaneously.

To express KOD1-GLDH gene, the resulting pTRP plasmid containing KOD1-GLDH is used to transform a host for use in the expression system. The host to be used in transformation may be *Escherichia coli* strain JM109 competent cell strain, for example. This *E. coli* JM109 strain is a cell strain which facilitates screening for recombinants, and can be used in the expression system. In these respects, this strain is suitable for use in the present invention. Transformation of the *E. coli* JM109 strain with the pTRP plasmid containing the KOD1-derived GLDH gene fragment is performed by Hanahan's calcium chloride method.

*E. coli* transformed with the KOD1-GLDH gene is cloned by forming colonies on an ampicillin-containing LB culture medium agar plate. To confirm whether the cloned *E. coli* has been transformed with the KOD1-GLDH gene, sequence analysis of some clones is made.

Then, fed-batch culture is performed using the *E. coli* transformed with the target gene. Methods of culture generally include batch culture and continuous culture. The former method cultures in a constant amount of culture medium. The latter method involves inflow of a culture medium at a constant rate, and simultaneous outflow of the old culture medium at the same rate. The latter method can culture the cells continuously in a constant amount of culture medium under as constant conditions as possible, and can separate the desired cells or substance from the old culture medium recovered. The fed-batch culture method is a further improvement on continuous culture which can cultivate cells at a higher density than continuous culture (Japanese Patent Public Disclosure: No. 252773/97). Its outline is as follows: A sterilized culture medium is incubated at 37° C., and inoculated with a preculture of the cells. The inoculated culture medium is maintained at 37° C., and spinner culture under aeration is performed, with the amount of dissolved oxygen being adjusted. Fresh medium in an amount corresponding to 10 to 15% of the culture medium present at the start of culture is persistently added at a progressively raised rate, with the turbidity of the cultured broth being monitored since the start of culture. According to this fed-batch culture, the culture broth in the same amount as the amount of fresh culture medium added is not drained, unlike continuous culture. By not draining the culture broth, the cell concentration of the culture broth is gradually increased over time. The culture medium used in the fed-batch culture may have the same composition as that of a culture medium for use in ordinary batch culture. Alternatively, the culture medium may further contain assimilable sources such as saccharides, vitamins, nitrogen sources such as amino acids, or other substances which promote the growth of the cells being cultured and/or the expression of the desired gene.

As described above, the use of the high expression plasmid pTRP, accompanied by fed-batch culture, enables the present invention to increase productivity markedly in comparison with the conventional methods, without the need to use drugs such as IPTG.

The present invention will now be described in detail by way of Examples, but it should be understood that the invention is not restricted thereby.

EXAMPLES

Example 1
Production of Recombinant Transformed With KOD1-GLDH Gene
Isolation of KOD1-GLDH Gene Pyrococcus sp. KOD1 strain (FERM P-15007) was static-cultured in a culture medium (18.70 g/L of 2216 Marine broth (Difco), 3.46 g/L of PIPES (Good's buffer), 0.73 g/L of $CaCl_2.2H_2O$, 13.38 g/L of NaCl, 0.52 g/L of KCl, 2.61 g/L of $MgCl_2.6H_2O$, 3.28 g/L of $MgSO_4.7H_2O$, 1 M $Na_2S.9H_2O$, and 6 g/L of sulfur powder) for 16 hours at 85° C. under anaerobic conditions. The KOD1 strain proliferated was recovered by centrifugation.

Separately, two types of degenerate primers, i.e., 5'-AAGCA(A/G)CTTG A(A/G)AGAGCTGC CCAATA-3' (forward primer, SEQ ID No. 3) and 5'-GT(A/G)TAAAC (A/G)T C(G/A)GGTGCTGG (A/G)ATGTC-3' (reverse primer, SEQ ID No. 4) were prepared based on a highly homologous portion of the amino acid sequence of GLDH from other previously reported archaebacteria, and the sequence of Pfu-GLDH gene.

Polymerase chain reaction of genomic DNA prepared from the recovered cells was performed using the forward primer (SEQ ID No. 3) and the reverse primer (SEQ ID No. 4) to amplify a targeted band of about 1.4 kbp long. The PCR reaction was carried out in 30 cycles, with each cycle comprising denaturation for 60 seconds at 98° C., annealing for 30 seconds at 55° C., and polymerization for 60 seconds at 74° C. Then, 29 cycles of the reaction was performed, with each cycle comprising denaturation for 15 seconds at 98° C., annealing for 2 seconds at 55° C., and polymerization for 30 seconds at 72° C. The amplified fragment was used as a probe to screen a genomic DNA library from Pyrococcus sp. KOD1 strain by Southern hybridization using DIG DNA Labeling and Detection Kit (Boehringer-Mannheim, Germany). The sequence of the resulting genomic DNA fragment was analyzed by Sanger's dideoxy-mediated termination method using an automatic DNA sequencing system (ALF Express, Pharmacia Biochemical Inc., Uppsala, Sweden). The genomic DNA fragment was confirmed to be a GLDH gene (KOD1-GLDH, SEQ ID No. 1). The KOD1-GLDH gene was found to have homology of 83.6% to the presumed amino acid sequence (FIG. 1), and homology of 74.6% (FIGS. 2 and 3) to the DNA sequence, of Pyrococcus furiosus-derived GLDH (Pfu-GLDH).

Construction of Expression Plasmid Containing KOD1-GLDH Gene

PCR was performed by utilizing the resulting genomic DNA fragment as the template and using a forward primer containing a site for the restriction enzyme NcoI (5'-TGAAAGAAGG AGATATCCAT GGTCGAGATT GAC-CCGTTTG A-3', SEQ ID No. 5) and a reverse primer containing a site for the restriction enzyme BamHI (5'-AAAGGGATCC GAAATCACTT CTTCACCCA-3', SEQ ID No. 6). As a result, a KOD1-GLDH gene fragment having NcoI/BamHI restriction enzyme sites at each end, respectively, was prepared. The PCR reaction was carried out in 30 cycles, with each cycle comprising denaturation for 60 seconds at 98° C., annealing for 30 seconds at 55° C., and polymerization for 60 seconds at 74° C. When the KOD1-GLDH gene fragment was to be ligated to expression vector pTRP, a synthetic linker oligonucleotide having the sequence 5'-GAATTCATGT ATCGCGATTT AAATAAG-GAG GAATAACCCA TGG-3' (SEQ ID No. 7) and including an EcoRI restriction enzyme site and an NcoI restriction enzyme site was caused to participate. That is, the NcoI-BamHI restriction enzyme treated KOD1-GLDH gene fragment, the EcoRI-NcoI restriction enzyme treated linker, and an EcoRI-BamHI restriction enzyme treated plasmid fragment were mixed, and ligated together simultaneously. Ligation was performed using DNA ligation kit Ver. 2 (TaKaRa, Japan) in accordance with an operating guide attached to the kit.

The resulting PTRP incorporating KOD1-GLDH gene was used to transform Escherichia coli JM109 competent cell strain (TaKaRa, Japan). Colonies of the resulting transformant were formed on an LB agar culture medium (Bacto-tryptone, 10 g/L; Bacto-yeast extract, 5 g/L; NaCl, 10 g/L; Bacto-agar, 15 g/L; pH 7.0) containing ampicillin (50 µg/ml). From among these colonies, the E. coli strain transformed with the exogenous plasmid was cloned. From the clones, the targeted E. coli transformant containing KODL-GLDH gene was selected, and named JM109/pTRP-KOD1 GDH (FERM P-16901). Sequencing showed the JM109/pTRP-KOD1 GDH to have the sequence SEQ ID No. 1. This finding ascertained that the JM109/pTRP-KOD1 GDH had been reliably transformed with KOD1-GLDH gene.

Example 2
Mass Production of KOD1-GLDH by Fed-batch Culture

KOD1-GLDH was mass produced using JM109/pTRP-KOD1 GDH. As a KOD1-GLDH expression medium for high density culture, New Brunswick Scientific Fermentor SF-116 (Edison, N.J., USA) was used. Culture was performed using 16 liters of the SF-116 medium, with the culture parameters, i.e., temperature, pH, agitation speed, and amount of aeration, being controlled to 37° C., pH 7.4, 800 rpm and 15 mL/min, respectively, by ML-4100 (multi-loop microprocessor controller). Adjustment of pH was made by addition of a 10% ammonia solution.

8 Liters of an LB culture medium (Bacto-tryptone, 10 g/L; Bacto-yeast extract, 5 g/L; NaCl, 10 g/L; pH 7.4; sterilized for 20 minutes at 120° C.) containing 25 mg/L ampicillin was prepared, and inoculated with culture broth (240 mL) of the transformant precultured overnight. The inoculum was spinner cultured for 2 hours at 37° C. with agiation.

Then, high density culture was performed for a sequent 10 hours with agitation under aeration (amount of aeration: 15 mL/min, agitation speed: 800 rpm). During this period, 2 liters of a fresh medium (10% glucose; 15% Bacto-yeast extract; 0.1% $MgSO_4.7H_2O$; 0.75% L-glutamic acid; 0.75% L-threonine; 0.04% L-tyrosine; 0.4% histidine; 0.4% methionine; pH 7.4) was continuously added at a progressively increased rate in accordance with a schedule shown in Table 1. Growth of the cells was confirmed by measuring the value of OD600.

TABLE 1

| Time after start of culture | Feeding rate | Amount of medium added |
|---|---|---|
| 0~2 hours | 0 mL/hour | 0 mL |
| 2~4 hours | 100 mL/hour | 200 mL |
| 4~6 hours | 200 mL/hour | 400 mL |
| 6~8 hours | 300 mL/hour | 600 mL |
| 8~10 hours | 400 mL/hour | 800 mL |
| | | Total: 2.0 liters |

Figure 5:
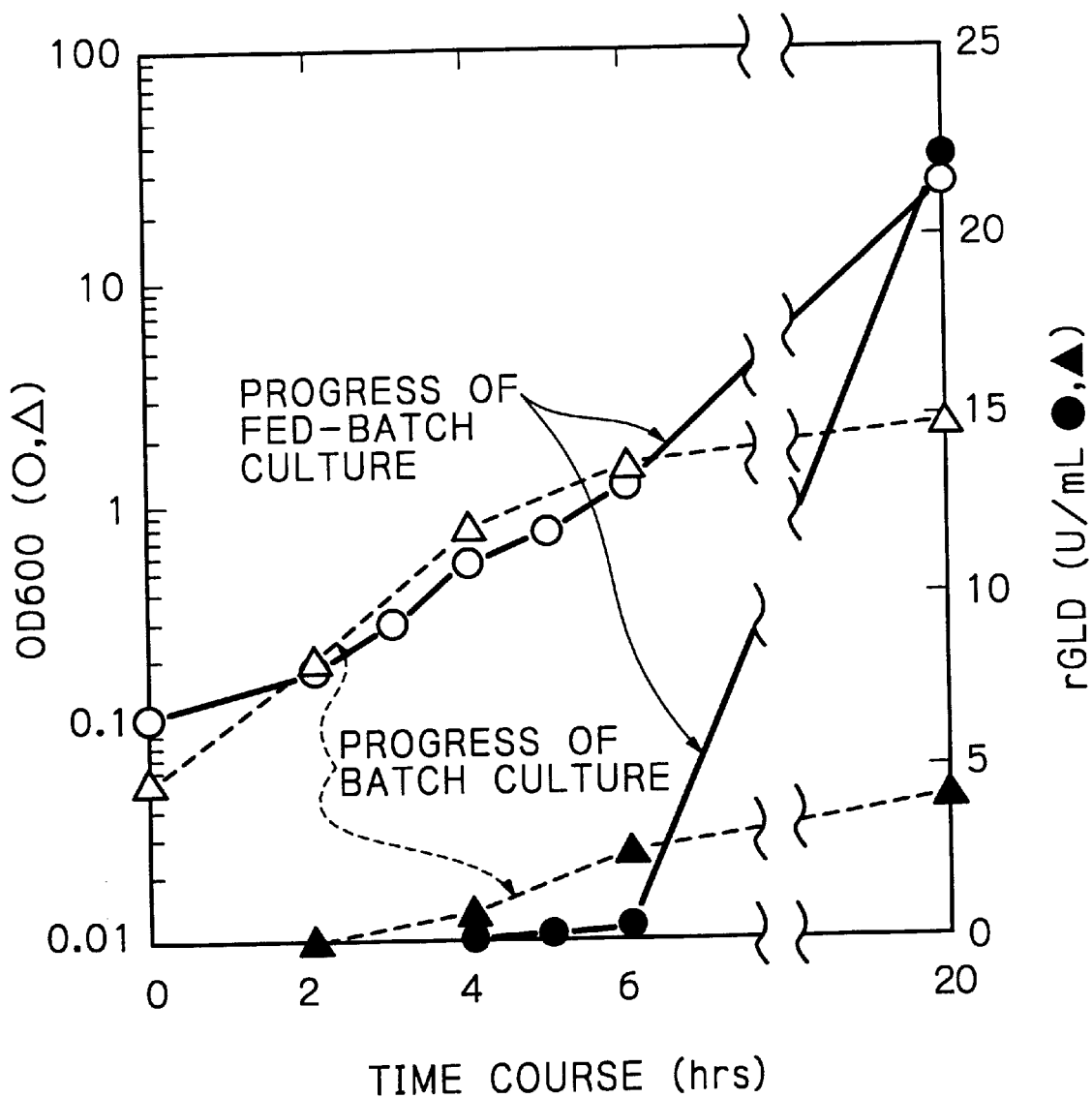
FIG. 5 shows the relationship between the turbidity of culture broth and the expression of recombinant KOD1-GLDH upon large scale culture by a fed-batch culture method in comparison with conventional batch culture.

Twelve hours after start of culture, the cells were harvested by centrifuging the cultured broth (11,000g×20 minutes). High density culture cells weighing about 500 g on a wet weight basis were obtained. The values of OD600 with the fed-batch culture are shown in FIG. 5 as compared with the values of OD600 obtained with conventional batch culture of JM109/pTRP-KOD1 GLDH (in FIG. 5, ○ for fed-batch culture, and Δ for batch culture).

The expression of recombinant GLDH upon fed-batch culture was compared with the expression of recombinant GLDH upon batch culture. Comparison showed that a nearly 5-fold increase in culture productivity at completion of culture was achieved by fed-batch culture (in FIG. 5, ● for fed-batch culture, and ▲ for batch culture).

Example 3
Purification and Physicochemical Properties of KOD1-GLDH Produced by Fed-batch Culture
Purification of KOD1-GLDH KOD1-GLDH was purified from the recovered fed-batch culture cells. The recovered cells were ground with a Dynomill to obtain an extract. The extract was heat treated for 20 minutes at 70° C. to remove $E.\ coli$. The heat treated $E.\ coli$-free extract was centrifuged to remove the precipitate. Then, the supernatant was subjected to ion exchange chromatography using DEAE-Sepharose CL6B gel (Pharmacia). This sample was eluted with a salt concentration gradient of 0 to 0.5 M NaCl. A main fraction of KOD1-GLDH targeted was recovered with 0.2 M NaCl.

Then, the fraction recovered was subjected to hydrophobic chromatography using phenyl-Sepharose CL4B gel (Pharmacia). This sample was eluted with a concentration gradient of 1 to 0 M ammonium sulfate. The targeted recombinant KOD1-GLDH came out at a concentration of 0.5 M ammonium sulfate.

The purified enzyme preparation was measured for activity. The enzymatic activity was measured as specific activity, with the $NADP^+$ output of 1 μmol/min at 37° C. as one unit. That is, enzymatic reaction was performed using a substrate reaction mixture containing 100 mM of TEA-HCl buffer (pH 8.0), 5 mM of 2-oxoglutaric acid, 0.2 M of $NH_4Cl$, and 0.3 mM of NADPH. The amount of $NADP^+$ produced was measured by a decrease in absorbance at 340 nm. The enzymatic activity of the purified enzyme preparation finally obtained was found to be have a specific activity of 300 U/mg.

Physicochemical Properties of Recombinant KOD1-GLDH

The physicochemical properties of the purified enzyme preparation of recombinant KOD1-GLDH recovered are summarized in Table 2.

TABLE 2

| | |
|---|---|
| Molecular weight: | 290 kDa (by gel filtration; hexamer) |
| Operating temperature: | 10 to 90° C. |
| Operating pH: | 6 to 10 |
| Optimum pH: | 8 |
| Heat stability: | Not deactivated even after heat treatment performed for 20 minutes at 80° C. |
| pH stability: | 4 to 11 |
| Coenzyme selectivity: | 100% for NADPH (100% in Pfu-GLDH) 2% for NADH (0% in Pfu-GLDH) |

The above results show that the recombinant KOD1-GLDH of the present invention, unlike conventional Pfu-GLDH, has coenzyme selectivity for NADH.

Example 4
Assay of Urea Nitrogen (UN) in Sample by Use of Recombinant KOD1-GLDH

The UN concentration of a serum sample was measured using the KOD1-GLDH prepared in Example 3. Reagents for use in the assay were a first reagent and a second reagent. The first reagent was prepared by mixing 15 mM 2-oxoglutaric acid, 0.4 mM NADPH, and recombinant KOD1-GLDH (1 to 20 U/mL), and adjusting the mixture to pH 9.2. The second reagent was prepared by forming microbial urease into a solution (urease content: 10 U/ml) and adjusting it to pH 8.0.

In this Example, human pooled serum (Wako Pure Chemicals, Japan) was used. This human pooled serum is available as two types of samples different in the UN content, i.e., human pooled serum I (low concentration; containing 21 mg/dL of UN) and human pooled serum II (high concentration; containing 50 mg/dL of UN). Pure water (2.5 μL) was added to 7.5 μl of each human pooled serum sample, and the mixture was used as an assay sample. The first reagent (240 μL) was mixed with the assay sample, and then 60 μL of the second reagent containing urease was mixed. Simultaneously with the mixing of the second reagent, urea in the serum sample began to decompose. Then, the resulting $NH_3$ was converted by the recombinant KOD1-GLDH in the first reagent into glutamic acid by the use of the coenzyme NADPH and the 2-oxoglutaric acid. The outline of this reaction is described by the following formula (2):

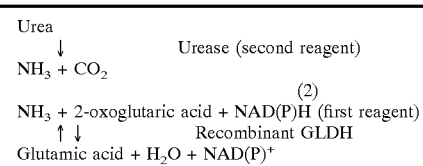

Figure 6:
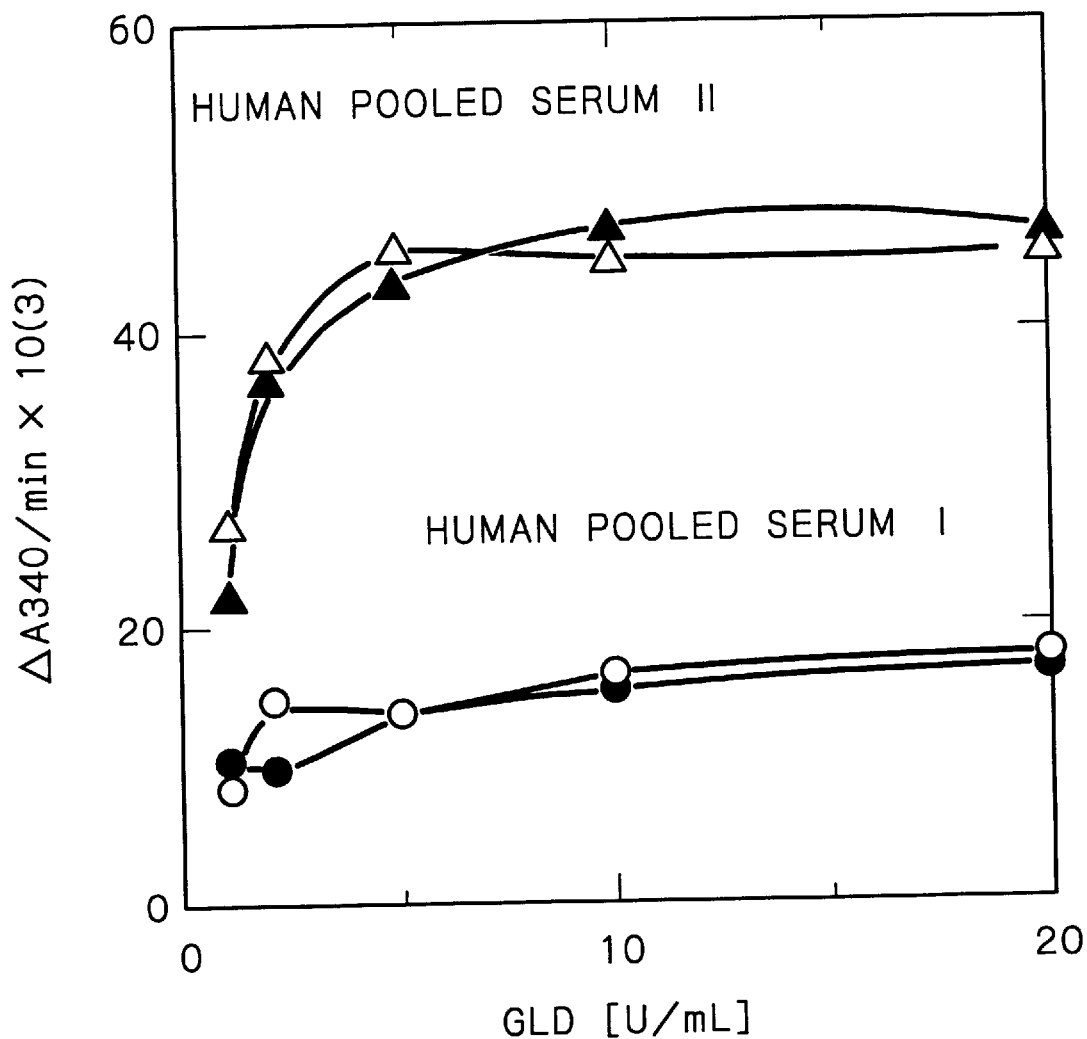
FIG. 6 shows the sensitivity of assay in a sample performed by the use of recombinant KOD1-GLDH produced by fed-batch culture, versus the amount of KOD1-GLDH added.

With this $NADP^+$ forming reaction as an indicator, the absorbance was measured at an assay wavelength of 340 nm by means of an automatic analyzer Cobaspherer (Roche, Swiss). After initiation of the reaction, changes in the absorbance at 340 nm were monitored. From the changes in absorbance during a 1-minute interval (i.e., ΔA340/min) from 2 minutes until 3 minutes after start of the reaction, the relation between the sensitivity of assay in the human pooled serum sample and the amount of recombinant KOD1-GLDH added was determined. The results obtained are compiled into FIG. 6. The same experiments were conducted using yeast-derived GLDH (Oriental Yeast Co., Ltd., Japan) as a control. In FIG. 6, ● and ▲ denote plots of the relationship between the serum UN assay sensitivity, found by the use of the KOD1-GLDH, and the amount of the GLDH added, while ○ and Δ denote plots of the relationship between the serum UN assay sensitivity, found by the use of the yeast GLDH, and the amount of the GLDH added. These results demonstrate that the recombinant KOD1-GLDH is comparable in performance for assay of UN in the sample to the commercially available GLDH derived from yeast.

Figure 7:
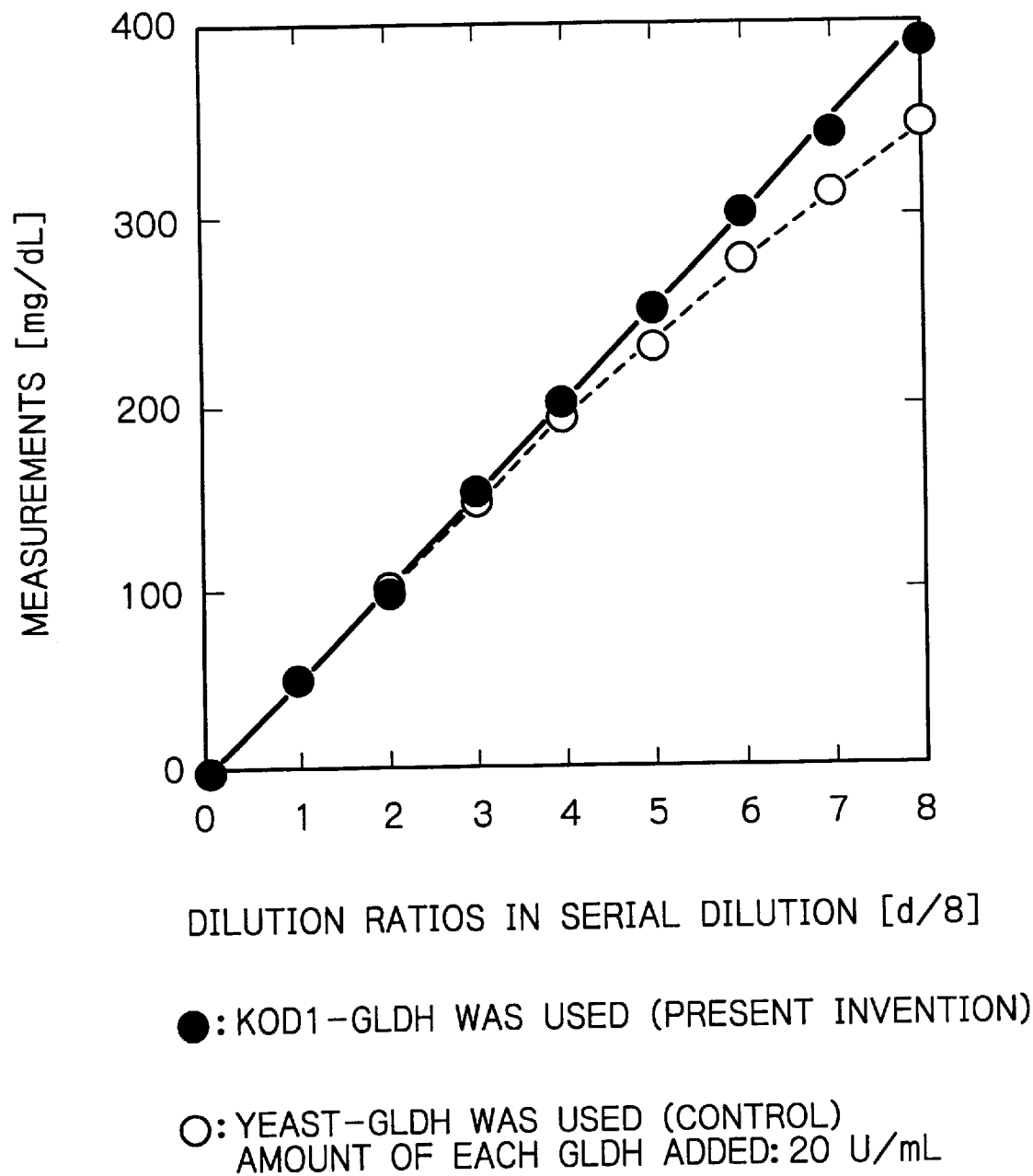
FIG. 7 shows the linear relationship between dilution ratios in serial dilution and urea nitrogen concentrations measured by the use of recombinant KOD1-GLDH produced by fed-batch culture.

In addition, the linearity of UN measurements in diluted samples by recombinant KOD1-GLDH versus the serial dilution ratios was investigated. A UN standard solution (400 mg/dL) was prepared, and serially diluted with 0.9% physiological saline to prepare respective diluted sample solutions. The relation between the actual UN concentrations calculated from the assay sensitivity (ΔA340/min) for each diluted sample solution and the dilution ratios in the serial dilution was examined. The results are shown in FIG. 7. In these experiments, the amount added of recombinant KOD1-GLDH in the first reagent was set at 20 u/ml, and a commercially available product derived from yeast was used as a control enzyme. Compared with the control yeast-derived GLDH, the recombinant KOD1-GLDH was found to be capable of performing UN assay linearly up to a higher concentration region.

Example 5

Assay of Urea Nitrogen (UN) by Use of NADH as Coenzyme

The UN concentration of a serum sample was measured using the KOD1-GLDH prepared in Example 3 by basically the same method as in Example 4. In this Example, two types of the first reagent were prepared, i.e., first reagent A prepared by mixing 15 mM 2-oxoglutaric acid, 0.4 mM NADH, and recombinant KOD1-GLDH (1 to 200 U/mL), and adjusting the mixture to pH 9.2, and first reagent B prepared by mixing 15 mM 2-oxoglutaric acid, 0.4 mM NADPH, and recombinant KOD1-GLDH (1 to 200 U/mL), and adjusting the mixture to pH 9.2. The second reagent was prepared in the same manner as in Example 4.

To 7.5 µL of commercially available human pooled serum (Wako Pure Chemicals, Japan), 2.5 µL of pure water was added, and the mixture was used as an assay sample. The first reagent A or B (240 µL) was mixed with the assay sample, and then 60 µL of the second reagent was mixed. Simultaneously with the mixing of the second reagent, the same reaction as described in Example 4 occurred to produce glutamic acid.

Figure 8:
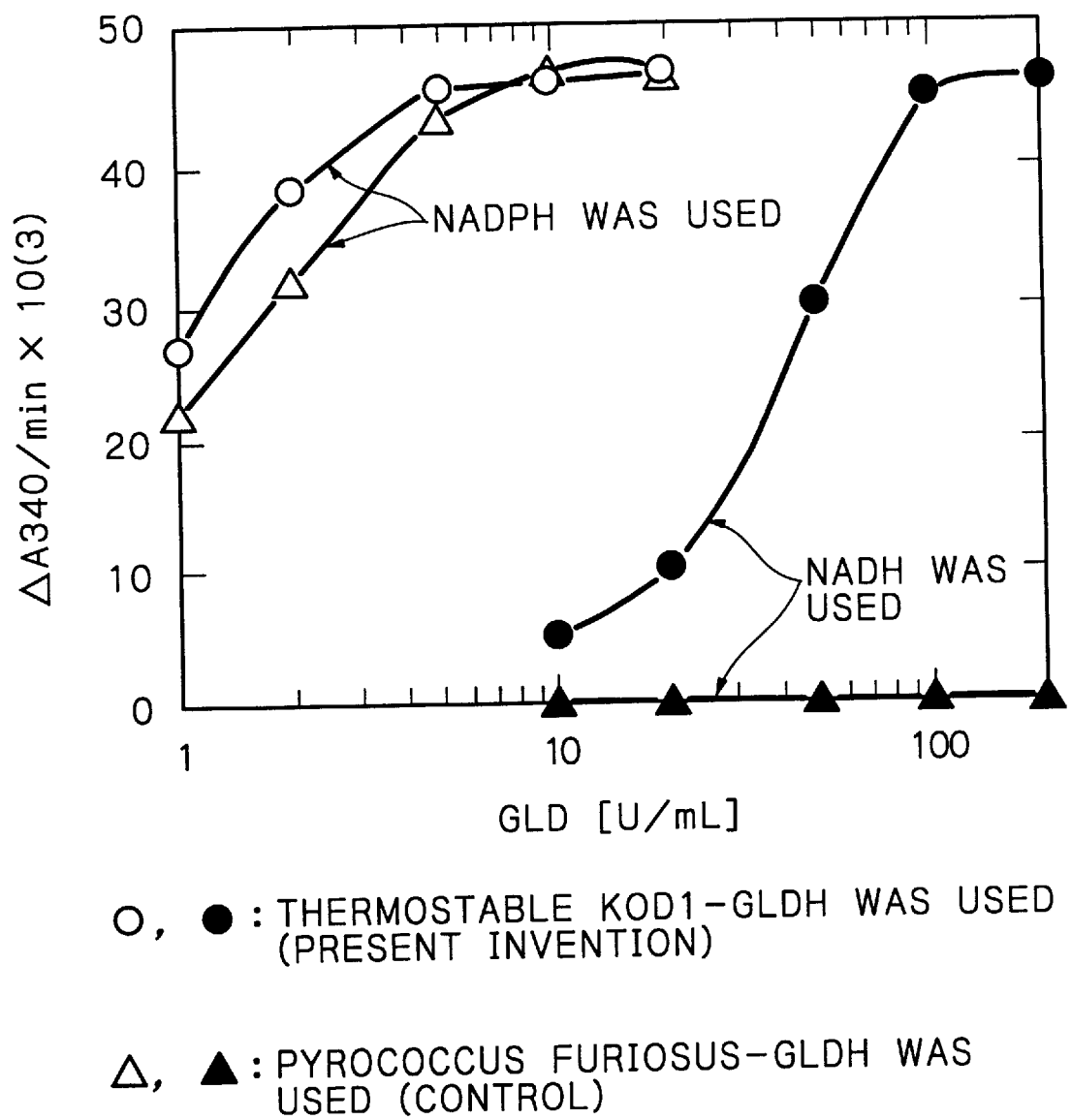
FIG. 8 shows enzymatic reaction curves of KOD1-GLDH and Pfu-GLDH depicted when NADH and NADPH were used as coenzymes.

With the $NADP^+$ forming reaction as an indicator, the absorbance was measured at an assay wavelength of 340 nm by means of the automatic analyzer Cobaspherer (Roche, Swiss). After initiation of the reaction, changes in the absorbance at 340 nm were monitored. From the changes in absorbance during a 1-minute interval (i.e., $\Delta A340/min$) from 2 minutes until 3 minutes after start of the reaction, the relation between the sensitivity of assay in the human pooled serum sample and the amount of recombinant KOD1-GLDH added was determined. The results obtained are compiled into FIG. 8. The same experiments were conducted using Pfu-GLDH, which specifically uses NADPH as a coenzyme, as a control. The results are also shown in FIG. 8. In FIG. 8, ● represents the results obtained from the experiments conducted by use of KOD1-GLDH as an enzyme and NADH as a coenzyme, ○ represents the results obtained by use of KOD1-GLDH and NADPH, ▲ represents the results obtained by use of Pfu-GLDH and NADH, and Δ represents the results obtained by use of Pfu-GLDH and NADPH. These results demonstrate that the use of KOD1-GLDH, unlike the use of Pfu-GLDH, permits the same UN assay as done through the use of NADPH, even when NADH is used as a coenzyme.

Figure 9:
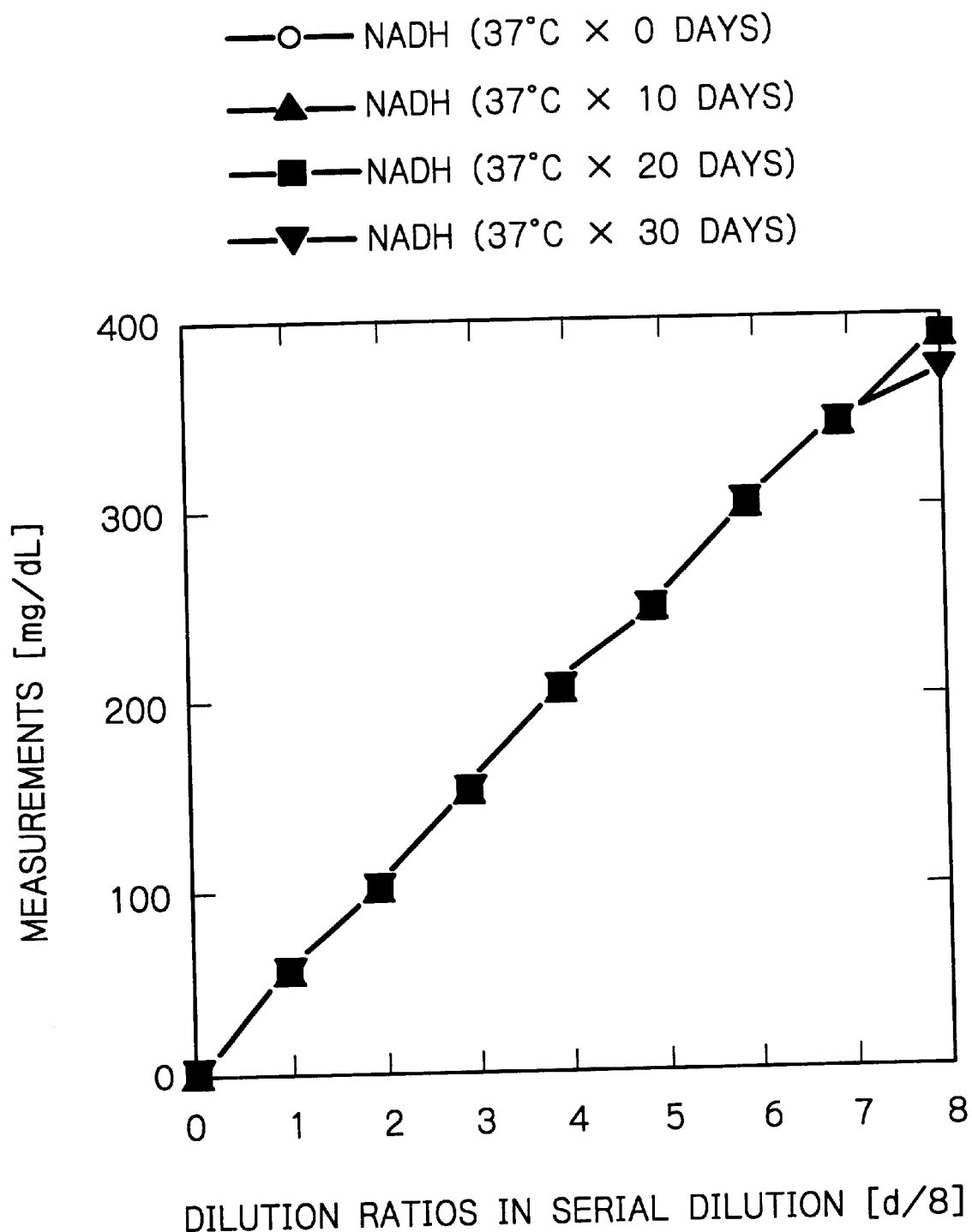
FIG. 9 shows the stability of a reagent kit comprising KOD1-GLDH, and NADH as a coenzyme, during long-term storage at room temperature.
Figure 10:
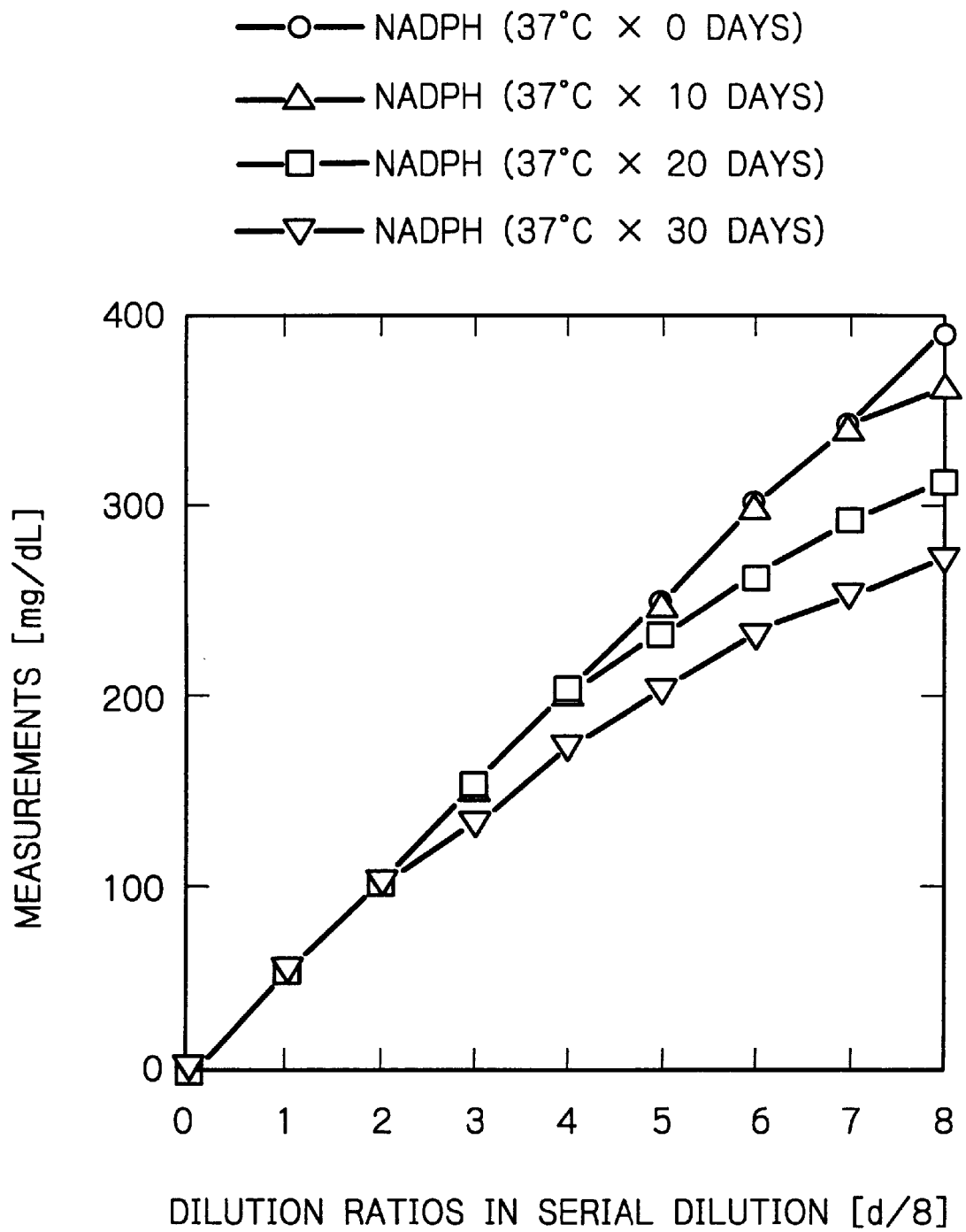
FIG. 10 shows the stability of a reagent kit comprising KOD1-GLDH, and NADPH as a coenzyme, during long-term storage at room temperature.

In addition, the linearity of UN measurements in diluted samples by recombinant KOD1-GLDH versus the serial dilution ratios was investigated as a comparison between the use of NADH and the use of NADPH as coenzymes. A UN standard solution (400 mg/dL) was prepared, and serially diluted with 0.9% physiological saline to prepare respective diluted sample solutions. The relation between the actual UN concentrations calculated from the assay sensitivity ($\Delta A340/min$) for each diluted sample solution and the dilution ratios in the serial dilution was examined. The results are shown in FIGS. 9 and 10. In these experiments, the amount added of recombinant KOD1-GLDH in the first reagent was set at 200 U/ml in the case of first reagent A (using NADH as a coenzyme), or 20 U/ml in the case of first reagent B (using NADPH as a coenzyme). The linearity of the UN measurements versus the series of dilution ratios was compared in both these cases using the different coenzymes upon long-term storage at room temperature. The results of experiments show that the use of NADH as a coenzyme (FIG. 9) provides more stable reproducibility than the use of NADPH as a coenzyme (FIG. 10) upon long-term storage. In light of these findings, a combination of NADH and KOD1-GLDH can provide a reagent for assay of UN in a biological sample, the reagent having higher solution-form storage stability.

This invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

---

What is claimed is:

1. A process for producing a recombinant glutamate dehydrogenase protein by large scale culture, which comprises performing fed-batch culture of a microbial transformant, while continuously controlling the concentration of dissolved oxygen and/or continuously adding assimilable sources, vitamins and nitrogen sources, said transformant resulting from transformation with a recombinant glutamate dehydrogenase gene obtained from Pyrococcos sp. KODI strain.

2. The process of claim 1, wherein the transformant is prepared by transformation with a pTRP plasmid incorporating the recombinant glutamate dehydrogenase gene obtained from Pyrococcos sp. KODI strain.

3. A thermostable glutamate dehydrogenase gene encoding the thermostable glutamate dehydrogenase obtained from Pyrococcus sp. KODI strain and capable of using reduced nicotinamide adenine dinuleotide (NADH) as a coenzyme.

4. The thermostable glutamate dehydrogenase gene of claim 3 which encodes the thermostable glutamate dehydrogenase having an amino acid sequence designated as SEQ ID No.2 of the sequence listing.

5. The thermostable glutamate dehydrogenase gene of claim 3 which has a nucleotide sequence designated as SEQ ID No:1 of the sequence listing.

6. An expression plasmid comprising a thermostable glutamate dehydrogenase gene obtained from Pyrococcus sp. KODI strain and capable of using reduced nicotinamide adenine dinuleotide (NADH) as a coenzyme.

7. *Escherichia coli* transformed with the plasmid of claim 6 so as to express the recombinant glutamate dehydrogenase in a large amount.

* * * * *